US006485299B1

(12) United States Patent
Wildman (10) Patent No.: US 6,485,299 B1
(45) Date of Patent: Nov. 26, 2002

(54) ADAPTER AND METHOD FOR CONVERTING LINGUAL ORTHODONTIC TIE BRACKET INTO SELF-LIGATING BRACKET

(75) Inventor: Alexander J. Wildman, The Woodlands, TX (US)

(73) Assignee: Lingual Orthodontics, Ltd., The Woodlands, TX (US)

( * ) Notice: Subject to any disclaimer, the term of this patent is extended or adjusted under 35 U.S.C. 154(b) by 18 days.

(21) Appl. No.: 09/707,754

(22) Filed: Nov. 6, 2000

Related U.S. Application Data (63) Continuation-in-part of application No. 09/439,749, filed on Nov. 15, 1999, now Pat. No. 6,142,776.
(60) Provisional application No. 60/199,794, filed on Apr. 26, 2000.

(51) Int. Cl.[7] .................................................. A61C 7/00
(52) U.S. Cl. .......................................... 433/10; 433/14
(58) Field of Search ................................ 433/8, 10, 11, 433/13, 14, 17

(56) References Cited

U.S. PATENT DOCUMENTS

| | | | |
|---|---|---|---|
| 4,337,037 A | 6/1982 | Kurz | 433/8 |
| 4,443,189 A | 4/1984 | Wildman | 433/10 |
| 4,531,911 A | 7/1985 | Creekmore | 433/8 |
| 4,634,662 A * | 1/1987 | Rosenberg | 433/10 |
| 4,669,981 A | 6/1987 | Kurz | 433/8 |
| 5,094,614 A | 3/1992 | Wildman | 433/14 |
| 5,362,233 A * | 11/1994 | Thompson | 433/10 |
| 5,474,446 A | 12/1995 | Wildman et al. | 433/14 |
| 5,511,976 A | 4/1996 | Wildman | 433/10 |
| 5,613,850 A | 3/1997 | Wildman et al. | 433/10 |
| 5,630,716 A * | 5/1997 | Hanson | 433/14 |
| 5,700,145 A | 12/1997 | Wildman | 433/10 |
| 5,782,631 A * | 7/1998 | Kesling et al. | 433/14 |
| 5,791,897 A | 8/1998 | Wildman | 433/10 |
| 5,857,849 A * | 1/1999 | Kurz | 433/10 |
| 5,863,199 A | 1/1999 | Wildman | 433/10 |
| 6,042,374 A | 3/2000 | Farzin-Nia et al. | 433/13 |
| 6,325,622 B1 * | 12/2001 | Kelly et al. | 433/11 |

* cited by examiner

*Primary Examiner*—Cary E. O'Connor
(74) *Attorney, Agent, or Firm*—Marger Johnson & McCollom, P.C.

(57) ABSTRACT

An adapter is configured to convert a non-self ligating lingual orthodontic bracket into a self-ligating bracket. The adapter is-removably attachable to the non-self ligating lingual orthodontic bracket and includes a self-ligating mechanism. According to a preferred embodiment, the bracket adapter includes a pin, a tube, and a lockwire. The pin is configured to be removably secured to the non-self ligating bracket. The tube is attached to or formed from an occlusal end of the pin. The lockwire is partially mounted within the tube and is capable of rotation between a ligating and a non-ligating position. In its ligating position, the lockwire securely retains an archwire within an archwire slot of the non-self ligating bracket using shear-resistant properties of the lockwire.

27 Claims, 5 Drawing Sheets

ADAPTER AND METHOD FOR CONVERTING LINGUAL ORTHODONTIC TIE BRACKET INTO SELF-LIGATING BRACKET

This application is a CIP of application Ser. No. 09/439,749, filed Nov. 15, 1999, now U.S. Pat. No. 6,142,776 and claims priority from provisional application Ser. No. 60/199,794 filed Apr. 26, 2000.

FIELD OF THE INVENTION

This invention relates generally to orthodontic devices. More specifically, this invention relates to orthodontic brackets and particularly self-ligating orthodontic brackets.

BACKGROUND OF THE INVENTION

Figure 1:
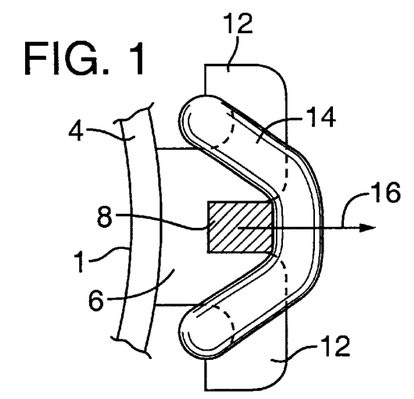
FIG. 1 is a side view of a conventional symmetrical dual-wing labial orthodontic bracket.
Figure 2:
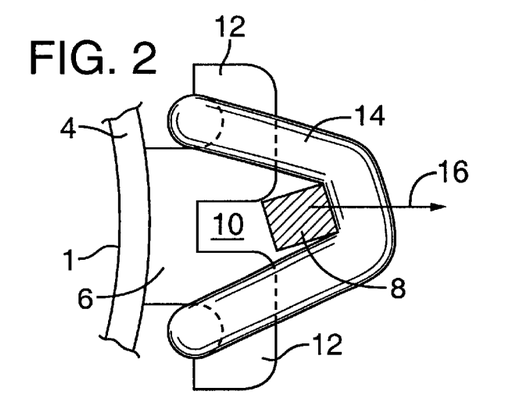
FIG. 2 is another side view of the conventional symmetrical dual-wing labial orthodontic bracket shown in FIG. 1 illustrating a force tending to remove an archwire from an archwire slot and also illustrating an O-ring's resistance of that force.

Several types of orthodontic brackets have been used in the prior art, including labial brackets and lingual brackets, which can each be either non-self ligating or self-ligating. As the name implies, labial brackets are positioned on the labial surfaces of a person's teeth. The most conventional type of labial bracket is a symmetric dual-wing bracket as shown in FIGS. 1 and 2. Referring to FIGS. 1 and 2, this bracket 1 has a bonding pad 4, a base member 6, and two opposing wings 12. An archwire slot 10 is located between the two wings 12 and receives an archwire 8 at a right angle to the plane of the bonding pad 4. After the archwire 8 is in place within the archwire slot 10, an O-ring 14 is placed around one of the wings 12 and then stretched over the opposing wing 12 in a single-tie configuration to retain the archwire 8 in place. Because it requires an O-ring to retain the archwire 8 in its slot 10, this bracket 1 is non-self ligating.

The single-tie O-ring configuration used with this bracket 1 allows the elastic tensile forces of both halves of the O-ring 14 to symmetrically oppose a force (represented by arrow 16) tending to remove the archwire 8 from the archwire slot 10. O-rings 14 must typically be replaced at least every six weeks because their elastomeric material degrades over time as a result of the chemical environment of the mouth. When it is time to replace the O-rings 14, the O-rings 14 are removed and replaced one at a time by simply disengaging the end portions of the O-ring 14 from the wings 12. The conventional labial bracket 1 is, therefore, fairly simple to use because the replacement of O-rings is straightforward.

Lingual brackets are attached to the lingual surfaces of a person's teeth. Lingual brackets are desirable because they are not readily noticeable to an outside viewer. Unlike the labial brackets described above, however, the conventional lingual brackets, as shown in FIGS. 3, 3A, 4, and 4A, are generally difficult or inefficient to use. Referring to FIGS. 3, 3A, 4, and 4A, a conventional lingual bracket 20 is asymmetric and comprises a bonding pad 24, a base member 36, and opposing occlusal (or incisal) and gingival wings 32 and 38, respectively.

The conventional lingual bracket also includes an archwire slot 30 located between the two wings 32 and 38. The archwire slot 30 of these brackets, however, is angled toward the gingival wing 38. The archwire slot 30 has an entrance in the direction of the gingival wing, opposing first and second walls, and a base located opposite the entrance in the direction of the base member 36. Examples are shown in U.S. Pat. Nos. 4,337,037 and 4,669,981 to Kurz. The gingival wing 38 can include an elongated extension with a knob end as shown in Kurz '981 or can be T-shaped to serve as a hook for inter-maxillary elastics. These lingual brackets are also non-self ligating because an O-ring 34 is used to secure an archwire 26 in the archwire slot 30.

Figure 3:
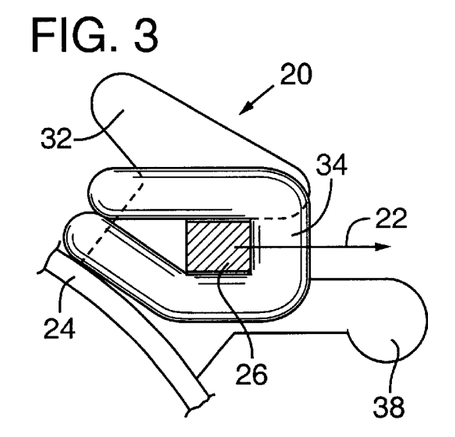
FIG. 3 is a side view of a conventional asymmetrical dual-wing lingual orthodontic bracket having a double-tie configuration.
Figure 4:
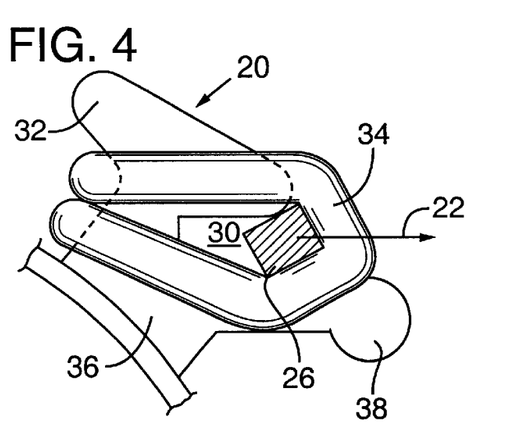
FIG. 4 is another side view of the conventional asymmetrical dual-wing lingual orthodontic bracket having the double-tie configuration shown in FIG. 3, further illustrating a force tending to remove the archwire from the archwire slot and also illustrating an O-ring's resistance of that force.

FIGS. 3 and 4 show the most typical tying arrangement of the conventional lingual bracket, i.e., double-tied. Referring to FIGS. 3 and 4, an O-ring 34 is generally double-tied around the archwire 26 of the conventional lingual bracket 20. In a double-tie configuration, the O-ring 34 must first be placed around the base 36 of the bracket 20. Only after the O-ring 34 is positioned around the base 36 is the archwire 26 inserted into the archwire slot 30 in a direction at an acute angle to the plane of the bonding pad 24.

A second end portion of the O-ring 34, located between the gingival wing 38 and the bonding pad 24, is then stretched over the gingival wing 38, around the archwire 26 and back over the occlusal wing 32, forming a substantially U-shaped O-ring configuration, as viewed from a side view. The tensile forces of both halves of the O-ring 34 retain the archwire 26 within the archwire slot 30 by nearly symmetrically opposing a force (represented by arrow 22) tending to disengage the archwire 26 therefrom.

Unfortunately, there are disadvantages with the double-tied lingual bracket of the prior art. First, as with labial brackets, the O-rings of lingual brackets must be replaced frequently. Unlike the single-tied labial brackets, however, the process for replacing the O-ring on a double-tied lingual bracket is complex. To replace the O-ring, the second end portion of the O-ring must first be stretched back over the occlusal and gingival wings such that the O-ring surrounds only the base member. Then, the archwire must be removed from the archwire slot. Only then can the old O-ring be completely removed from the bracket. Finally, a new O-ring must be attached using the steps described above for attaching the original O-ring. This process must be repeated for each of the lingual brackets needing O-ring replacement.

Another serious disadvantage with the use of double-tied conventional lingual brackets is that the O-ring must be stretched much further than that of the labial bracket. Excessive stretching further reduces the life of the O-ring. Furthermore, to accommodate this amount of stretching, the double-tied lingual bracket O-ring must be highly elastic. This increased elasticity adversely affects its tensile strength, and hence its ability to oppose forces that remove the archwire from its slot.

Figure 3A:
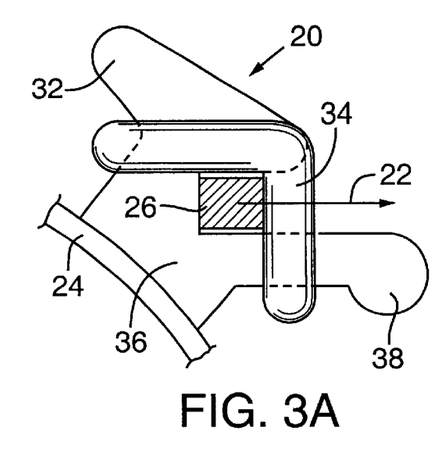
FIG. 3A is a side view of a conventional asymmetrical dual-wing lingual orthodontic bracket having a single-tie configuration.
Figure 4A:
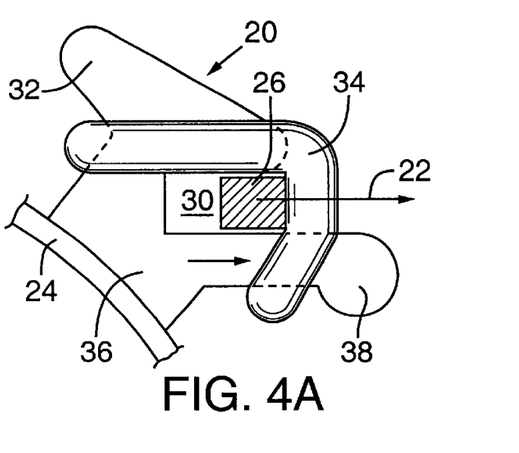
FIG. 4A is another side view of the conventional asymmetrical dual-wing lingual orthodontic bracket having the single-tie configuration shown in FIG. 3A, further illustrating a force tending to remove the archwire from the archwire slot and also illustrating the O-ring's resistance of that force.

To avoid some of these disadvantages associated with double tying the O-ring of the conventional lingual brackets, a single-tie configuration for the same brackets has been attempted. Although it is possible to single tie the archwire into the archwire slot of the conventional lingual bracket, using a single-tie configuration with the conventional lingual bracket is disadvantageous because it results in a very weak retaining force. FIGS. 3A and 4A show a conventional lingual bracket using a single-tie configuration.

As shown in FIGS. 3A and 4A, in a conventional lingual bracket 20 with a single-tie configuration, the O-ring 34 is placed over the gingival wing 38 and then stretched over the occlusal wing 32. In this configuration, a force (represented by arrow 22) acting to disengage the archwire 26 from the archwire slot 30 is only weakly opposed by the O-ring 34 for several reasons. First, only the portion of the O-ring 34 extending from the occlusal wing 32 has a tensile force which directly opposes movement of the archwire 26 away from the slot 30. The other portion of the O-ring 34, attached around the gingival wing 38 at approximately a right angle to the first portion, is free to slide along the gingival wing 38. It does not, therefore, provide any significant retaining force.

Further disadvantageous is the fact that the O-rings used to single tie the archwire into the archwire slot of the conventional lingual bracket must be replaced more frequently than those used in a double-tie configuration because they only have one portion of the O-ring that directly opposes the force tending to remove the archwire from the archwire slot. These drawbacks associated with conventional lingual brackets have made their use much less desirable than the labial brackets, despite the fact that many people prefer them aesthetically.

U.S. Pat. No. 4,531,911 ("Creekmore") discloses other single-tie bracket configurations for both labial and lingual applications. Creekmore, and the other dual-wing prior art brackets described above, rely solely on tensile properties of the O-ring to retain the archwire within the archwire slot. They do not contemplate the use of other properties of the O-ring which might aid in retaining the archwire within its slot.

The industry has been unable to provide to the orthodontic profession a simple, lingual bracket which allows easy O-ring attachment and replacement while providing sufficient retaining strength. Furthermore, the industry has relied solely on the tensile elastic properties of O-rings to retain the archwire within the archwire slot of both lingual and labial brackets. What the industry needs, therefore, is a lingual bracket which facilitates easy attachment and replacement of O-rings without compromising retaining strength. The profession would also be benefited by a method of retaining an archwire within the archwire slot of a lingual bracket which uses a more stretch-resistant O-ring.

Self-ligating brackets are one way to solve the difficulties that arise from the use of O-rings. Self-ligating brackets avoid the need for O-rings altogether by integrating a ligating member into the bracket itself. U.S. Pat. No. 6,042,374 (the '374 patent), for instance, discloses a self-ligating bracket that utilizes an integrated ligating member with at least one coil spring segment to secure the archwire within the archwire slot. The ligating member of the '374 patent is secured to either an occusal or gingival side of the bracket. After the archwire is positioned within the archwire slot, the ligating member is wrapped around the archwire and removably secured by one or more tie wings on the opposite side of the bracket. The coil spring segment allows the ligating member to stretch around the tie wings and bias the archwire in its slot.

Some advantages in lingual orthodontic brackets have been obtained by using camming closures to secure the archwire in the archwire slot, as for example, in U.S. Pat. Nos. 4,443,189; 5,511,976; 5,791,897; and 5,863,199. Each of these brackets have avoided the need for a double-tie O-ring configuration while still strengthening the retention of the archwire in the archwire slot over the conventional single-tie O-ring configuration. Generally, these configurations include a camming arm that closes to secure an archwire in the archwire slot. An O-ring can then be secured around the tie-wing and the camming arm to keep the arm in a closed position. Although these assemblies provide a fairly strong closure that is simpler to use than the double-tie O-ring configuration, these assemblies are fairly complex to manufacture and therefore expensive. They are also still not as simple to use as the single-tie O-ring configuration.

Self-ligating brackets offer distinct advantages over non-self ligating brackets in many treatment situations because of their ease of use. It is even more desirable, however, to be able to easily convert between non-self ligating and self-ligating brackets during treatment of a given patient to allow the orthodontist to choose the appropriate form of treatment at any given time. The ability to convert non-self ligating orthodontic brackets into self-ligating brackets would therefore be beneficial to the industry.

SUMMARY OF THE INVENTION

One object of the invention is to enable secure ligation of an archwire in a lingual bracket using a single-tie O-ring.

A first aspect of this invention is a lingual orthodontic bracket and a method of tying that makes tying elastomeric O-ring ligatures on a lingual orthodontic bracket much simpler and more effective. The bracket takes advantage of compression-resistant properties of an O-ring, in addition to its tensile elasticity, to secure an archwire within an archwire slot in a single-tie configuration. To do this, a T-shaped member of the gingival wing is positioned close enough to the archwire slot to provide a choke point that allows a cross-section of the O-ring to be compressed by a dislodging force.

Specifically, the bracket has a base member, which can be connected to a bonding pad. Opposing first and second, or occlusal and gingival, wings are connected to the base member to receive opposite end portions of an O-ring. An archwire slot is defined in the base member between the first wing and the second wing and is angled toward the second wing. An O-ring slot is defined transverse to the archwire slot in a lateral side of the base member between the base member and the second wing and is configured to receivingly engage a portion of the O-ring. The O-ring slot is arranged to form a choke point so that a force tending to remove the archwire from the archwire slot will compress the O-ring cross-sectionally between the archwire and the second wing.

In operation, the archwire is positioned within the archwire slot of the bracket, but a force tends to cause it to disengage from the archwire slot through an entrance thereof. The O-ring is attached between the first wing and the second wing such that the archwire is retained within the archwire slot by the O-ring. According to the preferred embodiment, the O-ring is stretched in a substantially L-shape configuration around the archwire from the first wing to the second wing, with a portion of the O-ring located in the O-ring slot. Thus configured, the O-ring opposes the force tending to remove the archwire from the archwire slot by both a tensile force and a compression resistant force.

A method for removably securing an archwire within an archwire slot of a lingual orthodontic bracket having a base member, opposing first and second wings, and an archwire slot positioned between the wings and canted toward the second wing is also provided. The method includes forming an O-ring slot on a lateral side of the base member between the base member and the second wing. An O-ring is removably attached around the first and second wings and over the archwire located within the archwire slot so that a force tending to remove the archwire from the archwire slot will be opposed by an elastic tensile force of the O-ring. The O-ring is further removably positioned within the O-ring slot such that the force tending to remove the archwire from the archwire slot is opposed by a cross-sectional compression resistant force of the O-ring.

Another object of this invention is to provide a self-ligating mechanism that can be added to a non-self ligating lingual bracket at any time during treatment.

In this aspect of the invention, a self-ligating mechanism replaces the O-ring to secure the archwire into the archwire slot of a lingual orthodontic bracket. The self-ligating mechanism includes an attachment mechanism for removably attaching the self-ligating mechanism to the bracket.

According to a preferred embodiment of the present invention, an occlusal-gingival auxiliary slot is milled, molded, or otherwise formed in the base of the bracket to receive an elongated attachment member, such as a pin, to which a self-ligating member, such as a lockwire or bale, is attached. After the bracket is mounted on the tooth, the attachment member is insertable into, and removable from, the auxiliary slot to permit the orthodontist to vary the mode of treatment, as desired. The self-ligating mechanism can be installed, left in place for a number of archwire changes, and then removed for subsequent treatments.

Although preferably configured for use with the lingual bracket described in the first aspect of this invention, this aspect of the invention can be implemented in other lingual brackets by including an occlusal-gingival slot in the base, and inserting an attachment member in a gingival direction into the slot. The attachment member carries a self-ligating member.

In the presently most-preferred embodiment, the pin is constructed of two layers configured to be inserted into the auxiliary slot. A base layer of the pin is configured having an end that protrudes from an occlusal end of the auxiliary slot of the bracket when inserted therein. A resilient layer of the pin is flexibly secured to the gingival end of the base layer of the pin so that it will fit inside the auxiliary slot under compression and allow for controlled sliding of the pin within the auxiliary slot. The protruding end of the base layer includes a hinging member securing a self-ligating member in rotational or hinged engagement with the base. The hinging member can be, for instance, an occlusally-located tube brazed onto an outward surface of the base layer in a mesio-distal orientation or an end of the base layer bent to form a tube shape.

In one embodiment, the self-ligating member is a U-shaped lockwire having a portion transverse to the pin member carried in the tube and having opposing arms extending from the transverse portion along opposite sides the bracket body. The lockwire rotates between a ligating and a non-ligating position. When the tube is brazed, the lockwire is inserted into the tube and then formed to shape. When the tube is formed from a bent end of the base layer, the lockwire can be pre-formed and snapped into place. In its ligating position, the opposing arms of the lockwire extend first along an outside of the bracket body and then bend inwardly into the ligature channels of the bracket to secure an archwire in an archwire slot. The lockwire has indentations that point toward the midline and seat into a gingival extenuation of the archwire slot when the lockwire is fully seated in its ligating position.

The combination of controlled sliding of the base member into the auxiliary slot and rotation of the lockwire permit the complex movement necessary to properly seat the lockwire in the ligature channels of the bracket. Also significantly, since the ends of the lockwire are positioned in the ligature channels in an orientation that is transverse to the archwire slot, a force tending to remove the archwire from its slot creates a shear force on the lockwire. Because the lockwire metal has a relatively high shear strength, this self-ligating mechanism provides very strong archwire retention.

BRIEF DESCRIPTION OF THE DRAWINGS

The foregoing and other objects, features, and advantages of the present invention will become more readily apparent from the following detailed description of a preferred embodiment of the invention which proceeds with reference to the accompanying drawings, in which.

DETAILED DESCRIPTION

Figure 5:
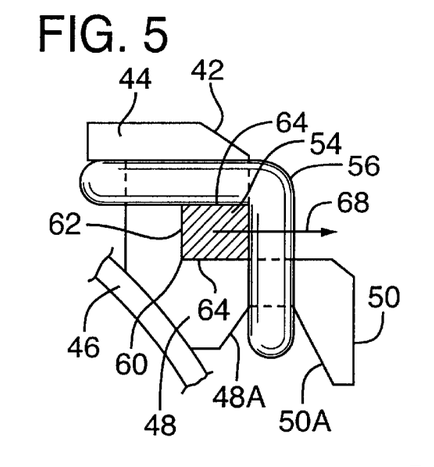
FIG. 5 is a side view of a lingual orthodontic bracket according to the invention using a single-tie O-ring configuration.
Figure 6:
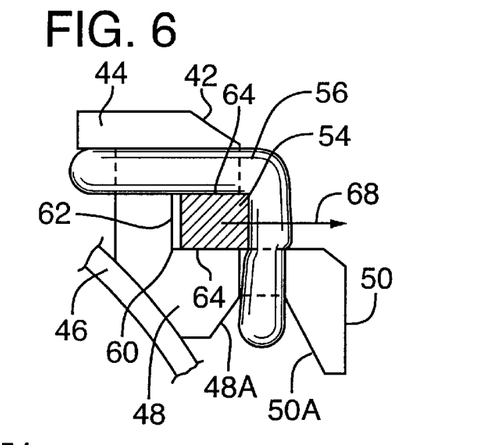
FIG. 6 is another side view of the lingual orthodontic bracket shown in FIG. 5 further illustrating a force tending to remove the archwire from the archwire slot and also illustrating an O-ring's resistance of that force using both tensile elastic and cross-sectional compression resistant properties thereof.
Figure 7:
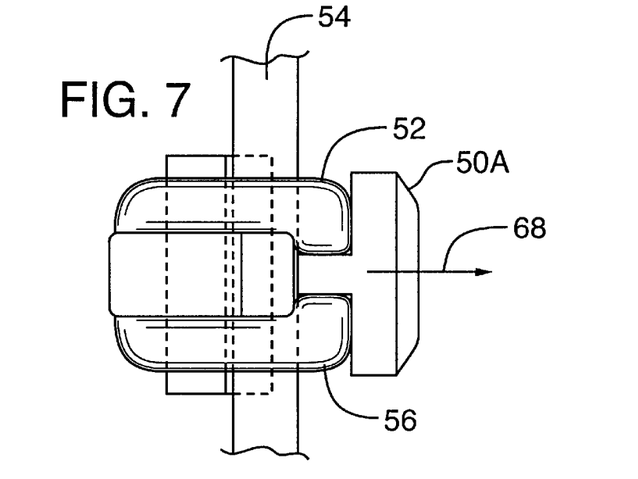
FIG. 7 is a plan view of the lingual orthodontic bracket shown in FIG. 5.

The first aspect of this invention will now be described with reference to FIGS. 5, 6, and 7. FIGS. 5 and 6 are side views, and FIG. 7 is a plan view, of the lingual orthodontic bracket according to a first aspect of this invention. Referring to FIGS. 5 and 7, a lingual orthodontic bracket 42 preferably includes a bonding pad 46 with a base member 48 attached to a lower surface thereof. Oppositely-directed first and second wings 44 and 50 are connected to the base member. The first (i.e., occlusal or incisal) wing 44 and second (i.e., gingival) wing 50 are configured to receivingly engage opposite end portions of an O-ring 56 in a single-tie configuration.

An archwire slot 60 is defined in the base member 48 between the two wings 44 and 50 in a direction angled toward the second wing 50. The archwire slot 60 has an entrance in the direction of the second wing between opposing first and second walls 64, and a base wall 62 located opposite the entrance in the direction of the base member. The base wall 62 is formed at an angle from the lower surface of the base member 46. The archwire slot 60 is configured to receive an archwire 54 through its entrance in a direction oriented at an acute angle to a plane of the bonding pad 46.

The lingual orthodontic bracket 42 is also provided with two O-ring slots 52 defined along opposite lateral sides of the base member 48 between the base member 48 and the second wing 50, where the base member 48 connects to the second wing 50. The O-ring slots 52 of the preferred embodiment are defined transverse to the archwire slot 60 and provide a choke point for the O-ring 56 as a result of their positioning in A relation to the archwire slot 60. Specifically, the O-ring slots 52 cause the connection between the base member 48 and the second wing 50 to appear as a T-shaped member when viewed in plan view, as shown in FIG. 7. The T-shaped member is positioned close enough to the archwire slot 60 so that a cross-section of the O-ring 56 will be compressed between the archwire 60 and the second wing 50 as a result of a force (arrow 68) tending to remove the archwire 54 from its slot 60.

Specifically, in that embodiment, a portion of the O-ring 56 fits within each of the O-ring slots 52. A first wall 52A of the O-ring slot 52 is substantially aligned with the entrance of the archwire slot 60. A second wall 52B of the O-ring slot 52 is spaced apart from the first wall 52A in the direction of the second wing 50 by a predetermined distance 53 approximately equal to the cross-sectional width or diameter of the O-ring 56. Both the second wing 50 and the base member 48 can be provided with sloping surfaces 50A and 48A, respectively, to urge the O-ring 56 into the O-ring slots 52. Having the O-ring slot 52 positioned adjoining the entrance to the archwire slot 60 enables the compression resistant properties of the O-ring to resist a force tending to remove the archwire 54 from the archwire slot 60 as shown in FIG. 6. This arrangement of features also allows the O-rings to be significantly more resistant to stretching than those used in the double-tie configuration, because the O-rings need not be stretched nearly as far over the wings to secure the archwire in place.

In operation, the archwire 54 is inserted into and positioned within the archwire slot 60 through the entrance thereof. The archwire 54 has just slightly smaller dimensions than the archwire slot 60. The O-ring 56 is then placed over either the first wing 44 or the second wing 50 and stretched around the archwire 54 and over the opposing wing 50 or 44, respectively. The O-ring 56 is thereby removably engaged by the wings 44 and 50 in a single-tie configuration in a substantially L-shape when viewed from a side view (FIGS. 5 and 6). Portions of the O-ring are also thereby positioned within the O-ring slots 52.

FIG. 6 further illustrates the operation and advantages of the bracket of the first aspect of the invention and its method of use. Referring to FIG. 6, a force (represented by arrow 68) tends to remove the archwire 54 from the archwire slot 60. The O-ring 56 opposes that force 68 in two ways. First, as the archwire 54 attempts to disengage from the archwire slot 60, the O-ring 56 is stretched lengthwise. Because of its elastic material, the O-ring 56 desires to return to its original length and a tensile elastic force opposes the force 68. This bracket therefore utilizes the tensile elastic force of the O-ring to oppose the force 68 tending to remove the archwire 54 from its slot 60.

Secondly, as the archwire 54 attempts to disengage from its slot 60, it pinches the portions of the O-ring 56 located at the choke points created by second (or opposing) walls 52B of the O-ring slots 52. The O-ring 56 resists this compressive force and desires to return to its original shape. The cross-sectional compression resistant force created by the compression of the O-ring 56 against the opposing walls of the O-ring slots 52 thereby also opposes the force 68 tending to remove the archwire 54 from the archwire slot 60. Because the O-ring slots 52 are located on a different level than the archwire 54, the compression force asserted by the archwire on the O-ring is a shear-type compressive force. The lingual orthodontic bracket 42 may be formed in any way conventionally known in the art, such as by metal casting, but is preferably formed using a metal injection molding (MLM) technique.

Self-Ligating Conversion Member

Figure 8:
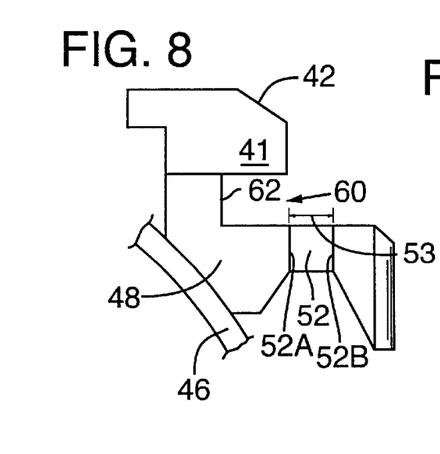
FIG. 8 is a side view of the bracket shown in FIG. 5.
Figure 9:
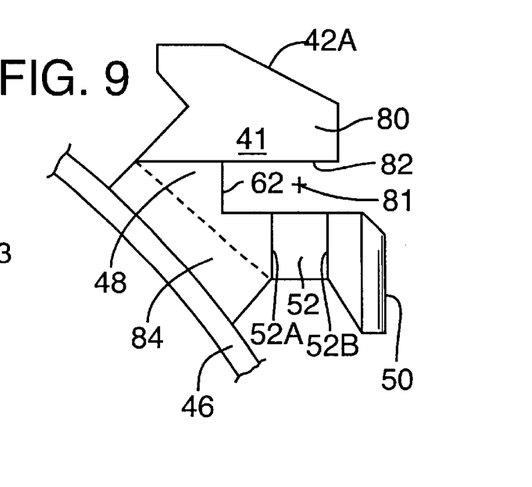
FIG. 9 is another side view of the bracket of FIG. 5 showing modifications to accept the self-ligating conversion pin of the preferred embodiment of this invention.

A preferred embodiment of the present invention will now be described with reference to FIGS. 9–13. FIG. 9 illustrates modifications to the bracket 42 of the first aspect of the invention, shown in FIG. 8, that enable incorporation of a self-ligating feature into the modified bracket 42A. Comparing FIGS. 8 and 9, an extension 80 and an auxiliary slot 84 are each added to the bracket 42 of the first aspect of the invention to facilitate incorporation of a self-ligating member into the modified bracket 42A. The extension 80 is added to the top wall of the archwire slot 41. The addition of the extension 80 provides an extenuation 81 of the archwire slot 62 past wall 52A of O-ring slot 52, preferably to wall 52B. The auxiliary slot 84 is formed in the underside of base member 48 and is configured to accept a pin 86 of the self-ligating mechanism shown in FIGS. 10 and 11. The pin 86 is configured so that it will fit into the auxiliary slot 84 between the base member 48 and the bonding pad 46 under a compression force and thereby allow for controlled sliding of the pin 86 within the auxiliary slot 84.

Figure 10:
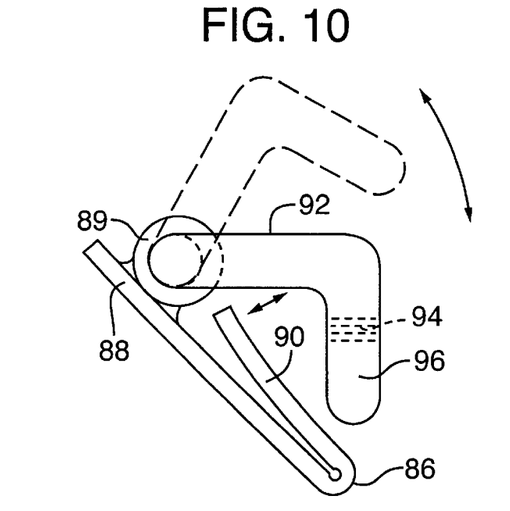
FIG. 10 is a side view of the self-ligating conversion pin according to a preferred embodiment of this invention.
Figure 11:
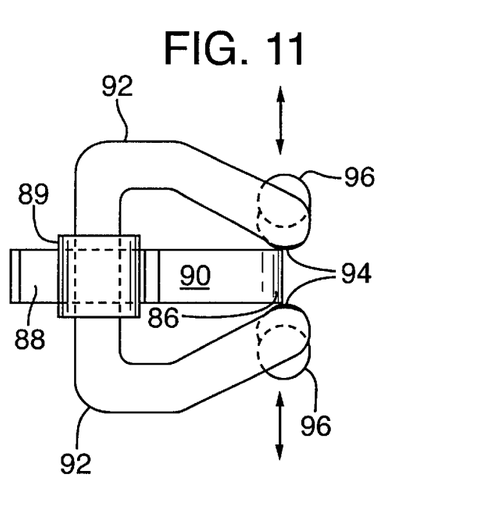
FIG. 11 is a plan view of the self-ligating conversion pin of FIG. 10.

Specifically referring to FIGS. 10 and 11, the pin 86 includes a base layer 88 and a resilient or leaf spring layer 90. The base layer 88 forms the base of the self-ligating mechanism and is substantially planar. The resilient layer 90 is formed above the base layer 88 and can be formed from a bent-over portion of the base layer 88 or from a separate layer. When the resilient layer 90 is formed from a segment of the base layer 88, the base layer is bent back onto itself at the gingival end at an angle of about 180°. The resilient layer 90 then curves gradually away from the base layer as it approaches the occlusal end. When the resilient layer 90 is a separate layer, the separate layer 90 is attached substantially planar with the base layer 88, such as by welding or other means, to the gingival end of the base layer 88 and extends gradually away from the base layer toward the occlusal end.

In each of these embodiments, the resilient layer 90 is compressed toward the base layer to allow it to be inserted into the auxiliary slot 84. Once inserted, the resiliency of this layer 90 urges it to return (at least substantially) to its original shape within the auxiliary slot 84. The relationship between the base layer 88 and auxiliary layer 90 permits the pin 86 to slide into and be removably retained within the auxiliary slot 84 by the resiliency of the resilient layer 90 and by friction.

When the pin 86 is fully inserted into the auxiliary slot 84, the base layer 88 protrudes occlusally from the slot 84. A tube 89 is formed on the base layer 88 at the protruding occlusal end in a mesio-distal orientation. The tube 89 can be brazed or otherwise attached to the base layer 88 or the occlusal end of the base layer 88 can be bent in a semicircle to form a tube. The tube 89 rotatably carries a transverse section of a lockwire 92, forming a hinge for the lockwire. When the tube 89 is brazed onto the base layer 88, the lockwire 92 can be inserted into the tube 89 and then formed into the appropriate shape. When the tube is formed from a bent portion of the base layer, the lockwire 92 can be pre-formed and snapped into place within the tube 89. The lockwire 92 can have a circular cross-section, as shown, or it can have any other cross-sectional shape, as desired.

Figure 12:
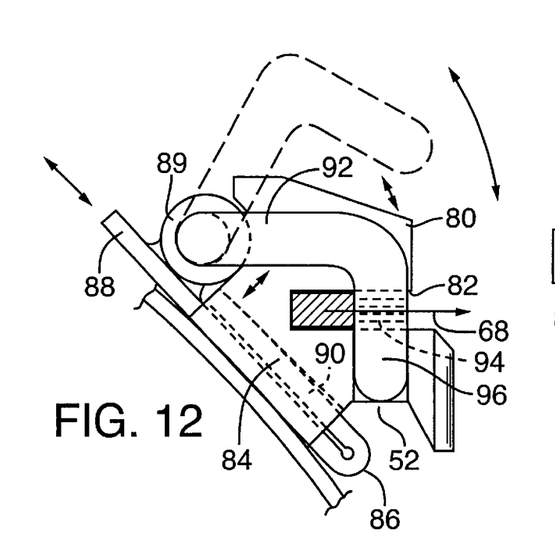
FIG. 12 is a side view of the self-ligating conversion pin of FIG. 10 with its lockwire in a ligating position to lock an archwire in place in the bracket of FIG. 9.
Figure 13:
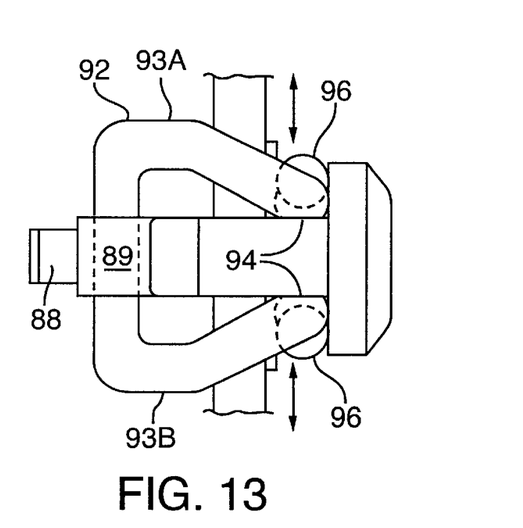
FIG. 13 is a plan view of the self-ligating conversion pin and bracket of FIG. 12.

Opposing arms 93A, 93B extend from each end of the transverse portion of lockwire 92. The lockwire 92 can swing between a ligating and a non-ligating position. When disposed in its ligating position, each arm 93A, 93B of the lockwire 92 extends alongside the archwire slot extension 80 of the bracket 42. At their distal ends, spaced away from the tube 89, the arms 93A, 93B of the lockwire 92 bend inwardly so that ends 96 of each of the arms 93A, 93B can be rotated into ligature channels 52 of the bracket to secure the archwire in the archwire slot 62.

The lockwire 92 also includes projections 94 on each of the arms 93A, 93B that are offset or point towards the midline of the bracket. The projections 94 form engagement sections of the arms 93A, 93B that seat into the space under the extension 80 of the top of the archwire slot when the lockwire 92 is fully closed. The curvature of the arms 93A, 93B toward the bracket body also provides a spring-like action that biases the arms toward each other, separated by a distance less than a width of the extension 80. This biasing action also helps secure the arms 93A, 93B in place. These arrangements keep the lockwire 92 fully seated in the ligature channels 52. Closing the lockwire 92 also retains the pin 86 in the auxiliary slot 84.

In this embodiment, the combination of controlled sliding of the pin 86 into the auxiliary slot 84 and the rotation of the lockwire 92 help permit the complex movement necessary to seat the lockwire 92 into the ligature channels 52. Since the ends 96 of the lockwire 92 are oriented in the channels 52 transverse to the archwire slot 62, a force (represented by arrow 68) tending to remove the archwire 54 from its slot 62 produces a compression or shearing force on the lockwire 92. Because the lockwire 92 is preferably formed of a metal (e.g., stainless steel) that has a relatively high shear strength, this ligating method is very secure.

It should be noted that although this invention has been described above with reference to a specific preferred embodiment thereof, numerous adaptations and modifications are within the level of ordinary skill in the art based on the foregoing disclosure. Several additional potential embodiments are described briefly below to demonstrate the breadth of the present invention.

First, although the pin and conversion method described above are preferably used with the bracket of the first aspect of this invention, this second aspect of the invention can be used to provide self-ligating functionality to a broad range of lingual brackets, in a variety of different ways. A conversion pin could, for example, be used to carry the coiled retention means taught by U.S. Pat. No. 6,042,374. Mounting a coil spring ligating member-such as the one shown and described in that patent—a conversion pin would increase the flexibility and usefulness of that invention.

Second, although a specific embodiment of the self-ligating mechanism has been shown and described, numerous other structures are also contemplated that provide the same functions of adapting a non-ligating lingual bracket to provide self-ligation. For example, the attachment mechanism could be a pin with a snap ring or any other attachment structure that permits the self-ligating mechanism to be removably secured to a bracket. Similarly, the ligating member itself can take virtually any structural form that can secure an archwire fully or partially within an archwire slot and is not limited to the lockwire assembly discussed above. The invention is similarly not limited to being made of any specific material or class of materials.

In another particular alternative embodiment, for example, instead of the lockwire 92 being configured with opposing arms 93A, 93B having separate, distinct ends 96, the arms 93A, 93B could be connected together at the gingival end to form a bale. In this configuration, the saddle-like gingival end of the lockwire 92 could snap over the extension 80. The extension 80 could be shortened slightly to permit this more easily. The lockwire 92 would thereby straddle the small portion of the choke and retain the archwire 54 in place. The lockwire 92 could be made of a flexible material that allows it to expand or contract. The lockwire 92 could also be open at the occlusal end and snap into indentations in any location along the bracket body.

In still another configuration, the lockwire 92 could be configured to snap over the entire choke member 50 and into the O-ring slot 52. Also, in any of the configurations, rather than projections 94 on the lockwire arms 93A, 93B, any other type of interference (indentations, tab and detent, etc.) between the lockwire and the bracket body could be used to secure the lockwire in position across the archwire slot. Furthermore, the lockwire 92 securing member, instead of being a tube 89, could be a recess having a structure that allows the lockwire 92 to do more than just pivot. The recess could, for example, be a non-circular slot to permit a lifting motion of the lockwire 92. Still other options include arranging the lockwire with an open, U-shaped occlusal end and providing hooks on ends of the lockwire 92. A channel in the bracket extension 80 could also be provided to direct a path for the removal of the lockwire 92 from the O-ring slot 52.

Various other configurations of the lingual bracket and conversion member are shown in FIGS. 14–22. Referring to FIGS. 14–18, the lingual bracket 100 is modified from bracket 42A by providing a locking groove or channel 102 along one, or preferably both, of its sides. This embodiment lacks the extension 80 of bracket 42A. The channel 102 receives detents 112 of the lockwire 110 to hold the lockwire in its ligating position. A crossbar 114 is provided on the lockwire 110 to help retain the archwire in its slot. Stub pins 116 on the lockwire 110 rotatably secure the lockwire 110 within a tube section 138 of a pin 130. The lockwire 110 of this embodiment has a rectangular cross-section.

Figures 14, 15:
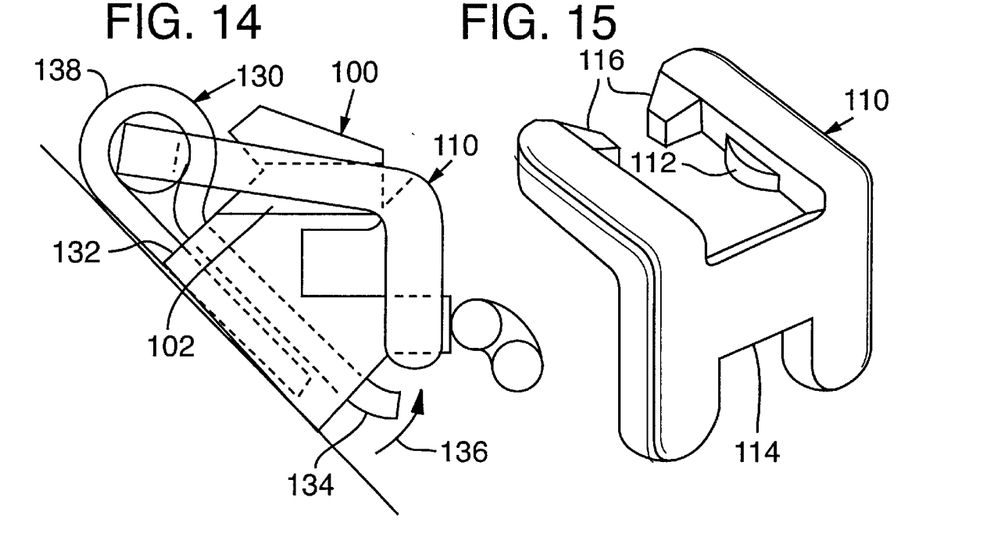
FIG. 14 is a side view of a lingual orthodontic bracket and self-ligating conversion pin according to another embodiment of the present invention.
FIGS. 15–17 are perspective, plan, and elevation views of a locking member of the self-ligating conversion member of FIG. 14.
Figures 16, 17, 18:
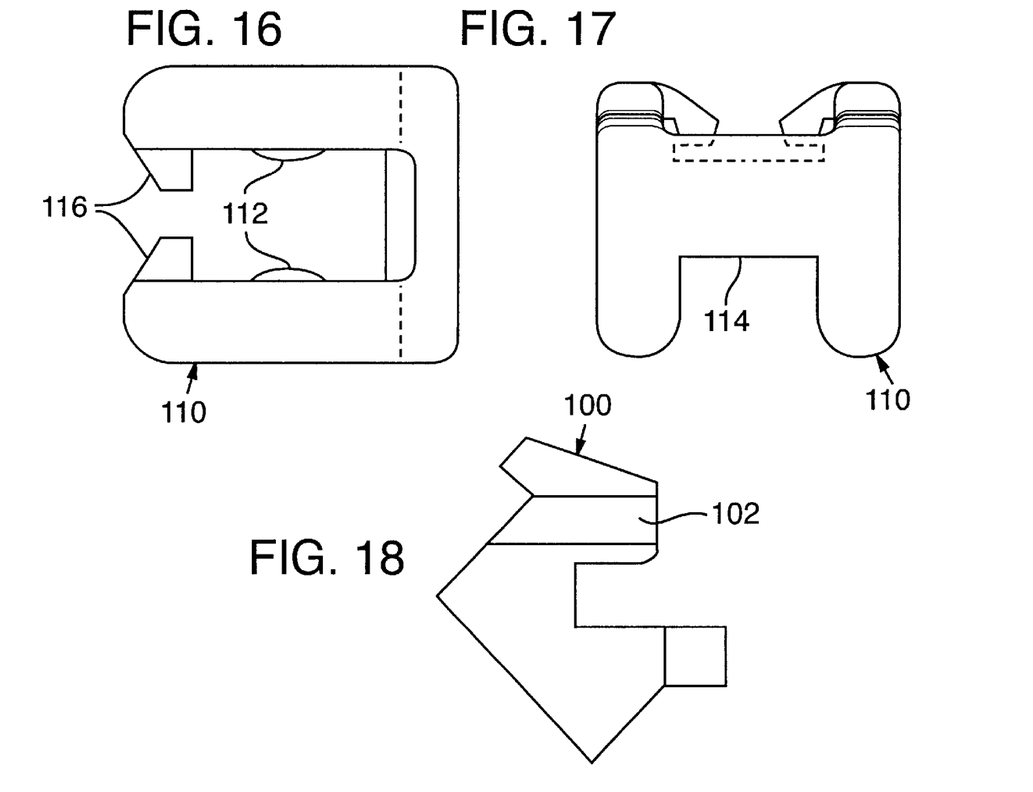
FIG. 18 is a side view of the lingual bracket shown in FIG. 14.
Figure 19:
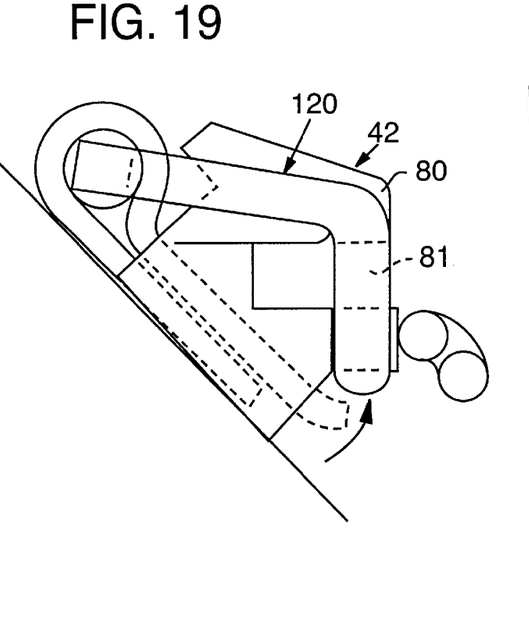
FIG. 19 is a side view of a lingual orthodontic bracket and self-ligating conversion member according to a still further embodiment of the present invention.
Figure 20:
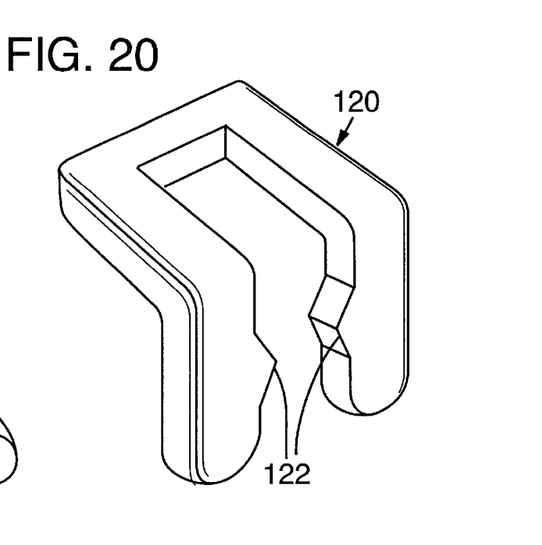
FIGS. 20–22 are perspective, plan, and elevation views of a locking member of the self-ligating conversion member of FIG. 19.
Figure 21:
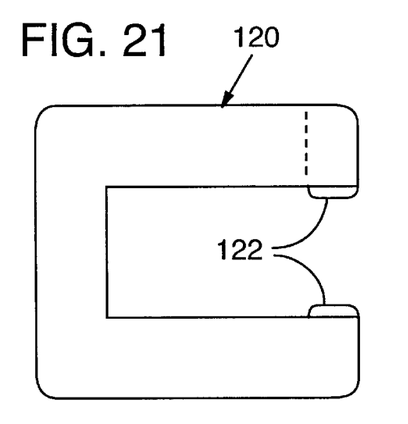
Figure 22:
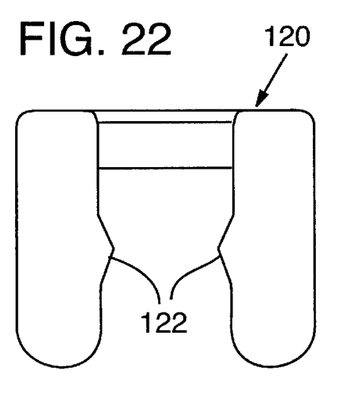

The pin 130 of this embodiment is formed of a single member bent to form a tube section 138 at its occlusal end and forming two substantially parallel layers—a base layer 132 and a resilient or biased layer 134—toward the gingival end. The resilient layer has an upwardly bent gingival end and tends to extend away from the base layer proceeding toward the gingival end (as represented by arrow 136) so that once the pin 130 is positioned within the auxiliary slot of the bracket, the resilient layer 134 holds the pin 130 in place within the slot.

Referring to FIGS. 19–22, in another embodiment, the lockwire 120 has a rectangular cross-section with detents 122 along the inside of each of its arms to engage beneath the extension 80 of the lingual bracket 42A. The lockwire detents 122 are seated within the area of the extenuated archwire slot 81, thereby seating the lockwire in operative relation with the bracket to retain an archwire within the archwire slot.

Numerous potential configurations of the pin 86 are likewise possible. For example, the pin could travel on tracks along an outside of the bracket body rather than within an auxiliary slot 84. The pin could also be configured integral with the self-ligating mechanism. For example, the pin and self-ligating mechanism could be formed from a contiguous piece, having a base member (and perhaps resilient member) that slides into the auxiliary channel and a resilient self-ligating member attached to the occlusal end and biased in a ligating position. The pin could thereby slide into the auxiliary slot causing the pin to slide over the bracket body until it becomes positioned in its ligating orientation within the O-ring slots 52.

Although the specific embodiment just described is preferably used with the foregoing lingual bracket, this embodiment and other embodiments of the invention can also be used to provide self-ligation functionality to a broad range of lingual brackets. Particularly, some types of brackets can be provided with a vertical (i.e., normal to the bonding pad rather than along the pad) auxiliary slot and configured to receive the pin and self-ligating member of this embodiment. Although some minor modifications to the self-ligating mechanism or to the lingual brackets may be necessary to allow these brackets to retain the self-ligating member in position across the archwire slot, such modifications are within the level of ordinary skill in the art and are covered by the appended claims.

Accordingly, having described and illustrated the principles of the invention based on a preferred embodiment thereof, it should be apparent that the invention can be modified in arrangement and detail without departing from these principles. I therefore claim all modifications and variations coming within the spirit and scope of the following claims.

What is claimed is:

1. A self-ligating mechanism for converting a non-self-ligating lingual orthodontic bracket into a self-ligating bracket said self-ligating mechanism comprising:
   a pin configured to be removably secured to a body of a lingual orthodontic bracket; and
   a lockwire swingably mounted on the pin and configured to move between a ligating position blocking an archwire slot in the bracket and a non-ligating position in which an archwire can be inserted in or removed from the archwire slot;
   the pin comprising a base member and a resilient member, wherein;
   the base member is substantially planar; and
   the resilient member is connected to the base member at a one end and is disposed away from the base member near an opposite end.

2. A self-ligating mechanism according to claim 1, in which the lingual orthodontic bracket includes an attachment slot formed in a base portion of the bracket and the pin is configured to be insertably received in the attachment slot.

3. A self-ligating mechanism according to claim 2, in which the attachment slot is formed in a base portion of the lingual orthodontic bracket approximately parallel to a bonding pad with an entrance on an occlusal end of the bracket.

4. A self-ligating mechanism according to claim 1, wherein the resilient member comprises a tube formed at an occlusal end of the base member.

5. A self-ligating mechanism according to claim 1, wherein the lockwire comprises a hinge attached to an occlusal end of the pin.

6. A self-ligating mechanism according to claim 1, wherein the bracket comprises an O-ring slot and wherein lockwire comprises:
   an arm extending from an occlusal end of the pin; and
   an end of the arm configured to be removably engaged in the O-ring slot of the lingual orthodontic bracket.

7. A self-ligating mechanism according to claim 1, wherein an arm of the lockwire comprises an end configured to be positioned within a ligature channel of the bracket to secure an archwire within an archwire slot of the bracket.

8. A self-ligating mechanism according to claim 1, wherein the lockwire is configured to resist a force tending to remove an archwire from an archwire slot of the orthodontic bracket using shear resistant properties of the lockwire when the lockwire is in the ligating position.

9. A self-ligating mechanism according to claim 1, wherein the lockwire comprises projections configured to seat into a gingival extenuation of an archwire slot of the orthodontic bracket when the lockwire is fully seated in a ligature channel of the bracket.

10. A self-ligating mechanism according to claim 1, wherein the lockwire has a substantially L-shaped configuration from a side view.

11. A self-ligating mechanism according to claim 1, wherein the lockwire has a substantially horseshoe-shaped configuration from a plan view.

12. An adapter for converting a non-self ligating lingual orthodontic bracket into a self-ligating lingual orthodontic bracket, said adapter comprising:
   an attachment pin configured to removably attach to a non-self ligating orthodontic bracket; and
   a self-ligating member attached to the attachment pin;
   the pin comprising a base member and a resilient member, wherein:
   the base member is substantially planar; and
   the resilient member is connected to the base member at a one end and is disposed away from the base member near an opposite end.

13. An adapter according to claim 12, wherein the self-ligating member is configured to retain an archwire within an archwire slot of the non-self ligating bracket using shear resistant properties of the self-ligating member.

14. An adapter according to claim 13, wherein the self-ligating member is a lockwire.

15. An adapter according to claim 14, wherein the lockwire comprises an arm configured to be removably secured within an O-ring slot of the non-self ligating orthodontic bracket.

16. An adapter according to claim 12, wherein tie self-ligating member is attached to the attachment pin by a hinge.

17. A self-ligating mechanism according to claim 12, wherein the lockwire comprises projections configured to seat into a gingival extenuation of an archwire slot of the orthodontic bracket when the lockwire is fully seated in a ligature channel of the bracket.

18. A lingual orthodontic bracket comprising:
a bonding pad for attaching said bracket to a tooth;
a base member connected to the bonding pad;
a tie wing connected to the base member for engaging an O-ring;
an archwire slot defined in the base member for receiving an archwire;
a choke; and
an auxiliary slot configured to removably receive a self-ligating mechanism;
the self-ligating mechanism including an adapter for converting the lingual orthodontic bracket into a self-ligating lingual orthodontic bracket, said adapter comprising:
an attachment pin configured to removably attach to the orthodontic bracket; and
a self-ligating member attached to the attachment pin;
the attachment pin comprising a base member and a resilient member, wherein:
the base member is substantially planar; and
the resilient member is connected to the base member at a one end and is disposed away from the base member near an opposite end.

19. An orthodontic bracket according to claim 18, wherein the archwire slot of the bracket fixer comprises an extended top wall.

20. An orthodontic bracket according to claim 18, wherein the self-ligating mechanism comprises a lockwire configured to move into a ligating position within the choke to secure an archwire within the archwire slot using shear resistant properties of the lockwire.

21. A self-ligating mechanism according to claim 18, wherein the lockwire comprises projections configured to seat into a gingival extenuation of an archwire slot of the orthodontic bracket when the lockwire is fully seated in a ligature channel of the bracket.

22. A self-ligating mechanism for converting a non-self-ligating lingual orthodontic bracket into a self-ligating bracket, said self-ligating mechanism comprising:

a pin configured to be removably secured to a body of a lingual orthodontic bracket; and
a lockwire swingably mounted on the pin and configured to move between a ligating position blocking an archwire slot in the bracket and a non-ligating position in which an archwire can be inserted in or removed from the archwire slot;
the lockwire being configured to resist a force tending to remove an archwire from an archwire slot of the orthodontic bracket using shear resistant properties of the lockwire when the lockwire is in the ligating position.

23. A self-ligating mechanism according to claim 22, wherein tile lockwire has a substantially L-shaped configuration from a side view.

24. A self-ligating mechanism according to claim 22, wherein the lockwire has a substantially horseshoe-shaped configuration from a plan view.

25. A self-ligating mechanism for converting a non-self-ligating lingual orthodontic bracket into a self-ligating bracket, said self-ligating mechanism comprising:
a pin configured to be removably secured to a body of a lingual orthodontic bracket; and
a lockwire swingably mounted on the pin and configured to move between a ligating position blocking an archwire slot in the bracket and a non-ligating position in which an archwire can be inserted in or removed from the archwire slot;
the lockwire comprising projections configured to seat into a gingival extenuation of an archwire slot of the orthodontic bracket when the lockwire is fully seated in a ligature channel of the bracket.

26. A self-ligating mechanism according to claim 25, in the lockwire has a substantially L-shaped configuration from a side view.

27. A self-ligating mechanism according to claim 25, wherein the lockwire has a substantially horseshoe-shaped configuration from a plan view.

* * * * *

UNITED STATES PATENT AND TRADEMARK OFFICE
CERTIFICATE OF CORRECTION

PATENT NO.    : 6,485,299 B1
DATED         : November 26, 2002
INVENTOR(S)   : Wildman It is certified that error appears in the above-identified patent and that said Letters Patent is hereby corrected as shown below:

Column 7,
Line 29, "in A relation" should read -- in relation --;

Column 13,
Line 29, "bracket fixer comprises" should read -- bracket further comprises --;

Column 14,
Line 36, "claim 25, in" should read -- claim 25, wherein --.

Signed and Sealed this

Twenty-second Day of April, 2003

JAMES E. ROGAN
*Director of the United States Patent and Trademark Office*